United States Patent [19]

Ickinger

[11] 4,354,844

[45] Oct. 19, 1982

[54] BEHAVIORAL AND PSYCHOLOGICAL TEST INSTRUMENT

[76] Inventor: William J. Ickinger, 254 Terrace Ave., Apt. C-2, West Haven, Conn. 06516

[21] Appl. No.: 199,737

[22] Filed: Oct. 23, 1980

[51] Int. Cl.³ ............................................. G09B 19/00
[52] U.S. Cl. .................................. 434/237; 52/645; 135/4 R; 160/351
[58] Field of Search ............... 434/237, 236, 250, 432, 434/433; 273/1 R, 1 G, 1 GE, 1 GF; D25/32, 93; 160/135, 351, 352; 135/3 R, 4 R, 5 B; 52/79.5, 645, DIG. 10

[56] References Cited

U.S. PATENT DOCUMENTS

| | | | |
|---|---|---|---|
| D. 172,987 | 9/1954 | Quigley | 273/1 A X |
| 1,291,758 | 1/1919 | Buck | 135/4 R |
| 1,730,267 | 10/1929 | Chittim | 135/4 R |
| 2,301,089 | 11/1942 | Stevens | 135/3 R |
| 2,530,765 | 11/1950 | Greenup | 135/4 R |
| 3,368,575 | 2/1968 | Besonen | 135/4 R |

FOREIGN PATENT DOCUMENTS

| | | | |
|---|---|---|---|
| 977719 | 11/1950 | France | 434/250 |
| 1313222 | 11/1962 | France | 273/1 A |

*Primary Examiner*—William H. Grieb
*Attorney, Agent, or Firm*—Mattern, Ware, Stoltz & Fressola

[57] ABSTRACT

An instrument for the study of certain aspects of individual and interpersonal human behavior is described. The instrument is a portable room in which the behavior of one or more people can be observed and statistically analyzed in such a way as to increase understanding of certain physical and psychological factors influencing human behavior. This portable room has a floor plan, in a preferred embodiment, in the shape of a regular hexagon 7.5 meters (approximately 24.6 feet) across its longest dimension. This hexagonal floor space is enclosed by six curtain walls supported by a framework that can be folded for convenient storage when not in use. The floor of the room is a flexible cloth or plastic sheet with a pattern of equilateral triangles inscribed on its surface. These features of the room or instrument are utilized to facilitate a statistical analysis that produces scientific results not obtainable by other methods.

18 Claims, 7 Drawing Figures

BEHAVIORAL AND PSYCHOLOGICAL TEST INSTRUMENT

BACKGROUND OF THE INVENTION

The invention relates primarily to psychological testing, and more particularly to (a) the manner in which various physical and psychological characteristics of people influence the way they use physical space in personal behavior and interpersonal interaction, and (b) the testing of various psychological and social-psychological theories by observation, by qualified personnel, of people engaged in structured activities or interpersonal interaction within the device.

Much of the prior research on how people use physical space in interpersonal interaction has been summarized by Irwin Altman and Anne Vinsel in a chapter titled "Personal Space—An Analysis of E. T. Hall's Proxemics Framework" in *Human Behavior and Environment*, eds. I. Altman and J. Wohlwill, Vol. 2, New York: Plenum, 1977. In this article factors that have been shown to influence interpersonal distancing and the use of personal space are divided into three categories—individual, interpersonal, and situational factors. Individual characteristics that emerge as significant in the existing research are summarized as follows.

In summary, research on individual characteristics and personal space suggests a framework based on the power, confidence, and control properties of the subject and the other participant. Low power in the subject is associated with increased distance from others, while confidence or power is associated with a willingness to be physically closer to others. Also, larger distances are maintained from a more threatening target person with whom one is interacting. These data correlate nicely with attraction and intrusion studies. That is, a positively valued person is approached more closely than a negatively valued person in the case of attraction studies, and a stranger who comes overly close is presumably threatening and is avoided, as shown in intrusion studies. (Altman and Vinsel, 1977, p. 229).

The significant interpersonal factors are similarly summarized in the following excerpt.

The samples suggests the importance of two major types of variables: similarity and acquaintance/attraction. First, people use closer distances when interacting with others who are similar rather than dissimilar in age, sex, status, etc. Second, and most frequently researched, people use less space when interacting with people whom they like, with whom they have had positive experiences, or with whom they are better acquainted, such as friends versus acquaintances versus strangers. Furthermore, the liking effect works both ways. That is, people sit or stand closer to those whom they like, and they are attracted to those close to whom they are forced to sit or stand. (Altman and Winsel, 1977, p. 213).

Effects of situational factors are not yet well defined, however, assuming that the most salient feature of the setting created by this instrument is its unfamiliarity, one may speculate that it will tend to evoke behavior reflecting generalized expectancies about the objects or people within it. Generalized expectancies have been discussed by Julian Rotter in an article titled "Some Problems and Misconceptions Related to the Construct of Internal Versus External Control of Reinforcement" in *Journal of Consulting and Clinical Psychology*, Volume 43, pp. 56–67, 1975 as follows.

Expectancies in each situation are determined not only by specific experiences in that situation but also, to some varying extent, by experiences in other situations that the individual perceives as similar. One of the determinants of the relative importance of generalized expectancies versus specific expectancies developed in the same situation is the amount of experience in the particular specific situation. These relationships are expressed in the formula below . . .

$$E_{s1} = f\left(E'_{s1} \& \frac{GE}{N_{s1}}\right).$$

In this formula $s_1$ represents the specific situation and N represents the amount of previous experience the individual has had in that situation. E represents expectancy; E' represents a specific expectancy; and GE represents generalized expectancy. Clearly, if the formula is correct, and there is considerable empirical evidence to support it, then the relative importance of generalized expectancy goes up as the situation is more novel or ambiguous and goes down as the individual's experience in that situation increases. (Rotter, 1975, p. 57).

This would suggest that the situational characteristics of the instrument would tend to draw out, and perhaps amplify, generalized expectancies because of its novel and ambiguous nature. Since such expectancies seem, at the limit of generality, to merge into what are more commonly called personality characteristics, it could be argued that the instrument will accentuate the effects of individual differences in personality and person-perception on spatial behavior.

OBJECTS OF THE INVENTION

An object of the invention is to provide an environment for individual behavior and interpersonal interaction which will tend to accentuate the effects of various physical and psychological characteristics of people acting within it upon interpersonal distancing and their use of physical space.

Another object of the invention is to provide an environment for individual behavior and interpersonal interaction which has spatial and temporal characteristics that permit precise and detailed analysis of behavior within it using analytical procedures developed specifically for use with the invention as well as other analytical techniques in general use in the study of human behavior.

Another object of the invention is to provide an environment for individual behavior and interpersonal interaction which is useful for training and/or diagnostic purposes.

Another object of the invention is to standardize this environment so that experiments or procedures performed in different specimens of the instrument may be directly compared.

Another object of the invention is to make the instrument portable, easily erected or disassembled, and capable of being stored in a relatively small space when not in use.

Other and more specific objects will in part be obvious and will in part appear hereinafter.

SUMMARY OF THE INVENTION

The invention comprises a room with a pattern inscribed on the floor having spatial and statistical properties which permit precise analysis of individual or interpersonal behavior acted out upon it in accordance with certain conditions specified by a qualified person.

Components of the invention, in its preferred embodiment, include (a) a jointed or collapsible framework to support the walls, (b) opaque "curtain" walls, and (c) the floor on which the pattern is inscribed. In a preferred embodiment illustrated in the figures accompanying this application the room is a portable, temporary structure which is erected within a larger room in an existing structure. The supporting framework is constructed of a lightweight, fireproof or fire-retardant material such as aluminum or treated wood, the walls are made of white cloth or flexible plastic sheeting treated for fire-retardancy, and the floor is made by heavy cloth such as canvas or alternatively of heavy plastic sheeting upon which the required pattern is inscribed (again the material is to be treated for fire-retardancy).

The specific embodiment of the invention described herein has a floor plan in the shape of a regular hexagon measuring 7.5 meters (approximately 24.6 feet) across its longest dimension. The framework supporting the curtain walls can be adjusted in height so that the curtain walls reach from floor to ceiling of whatever room the invention is set up in.

Advantages of the invention over other methods and techniques include its provision of a standardized environment (a) enabling human spatial behavior to be observed and analyzed more precisely and accurately than has previously been possible (b) enabling the results of many different experiments or procedures performed within the device to be directly compared, and (c) potentially permitting the discovery and interpretation of aspects of human behavior not measurable using other approaches or apparatus.

In addition to its primary purpose as an aid to basic psychological and social-psychological research, the invention may find application in such commercial areas as (a) product testing—for example, testing the effect of various perfumes or styles of clothing on interpersonal spatial behvior; (b) industrial design—for example, testing the effect of various light levels and lighting arrangements on interpersonal spatial behavior; (c) training and/or self awareness—for example, by providing an environment where the effects of various non-verbal behaviors on interpersonal interactions may be quantified, the device may prove useful in training individuals such as salespersons, actors or actresses, etc. in occupations where such behaviors are important; and (d) other fields where applied research on human behavior has commercial significance.

The invention accordingly comprises the features of construction, combination of elements, and arrangement of parts which will be exemplified in the construction hereinafter set forth, and the scope of the invention will be indicated in the claims.

THE DRAWINGS

The drawings furnished herewith illustrate a preferred embodiment of the present invention in which the above advantages and features are clearly disclosed as well as others which can be readily understood from the following description.

DETAILED DESCRIPTION

FIG. 1

Figure 1:
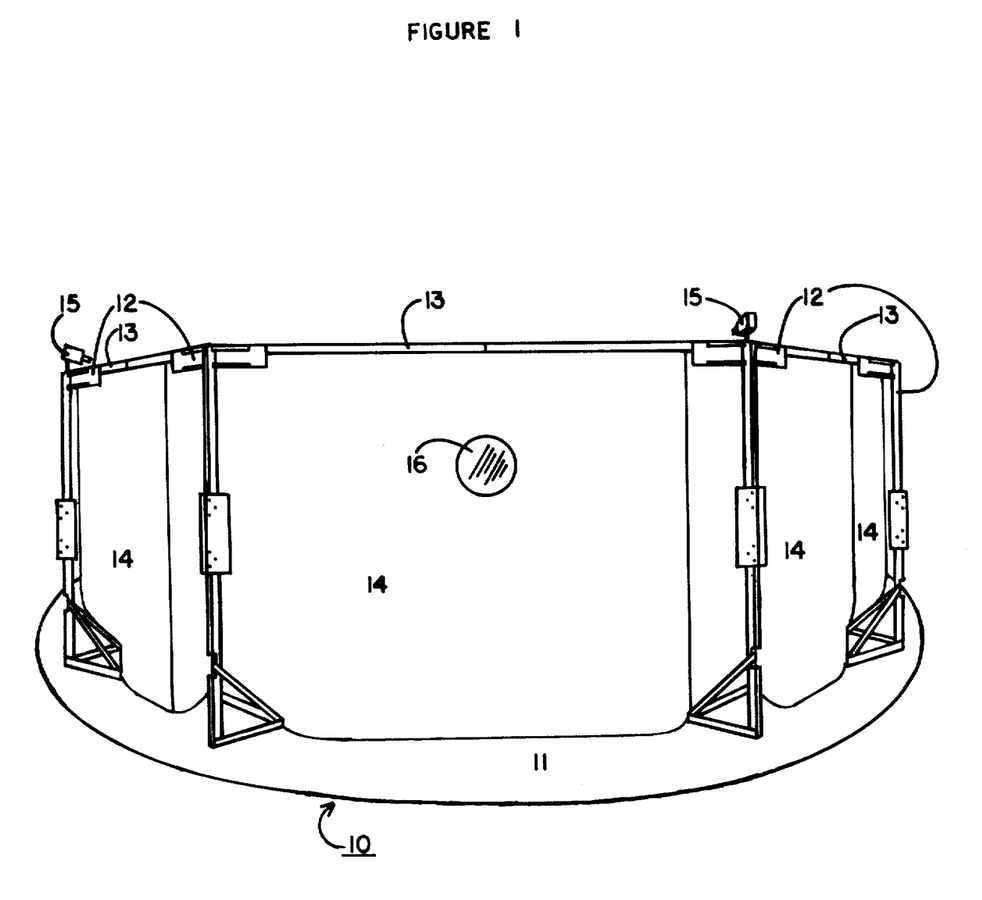
FIG. 1 is a side view, in perspective, of a preferred embodiment of the present invention.
Figure 2:
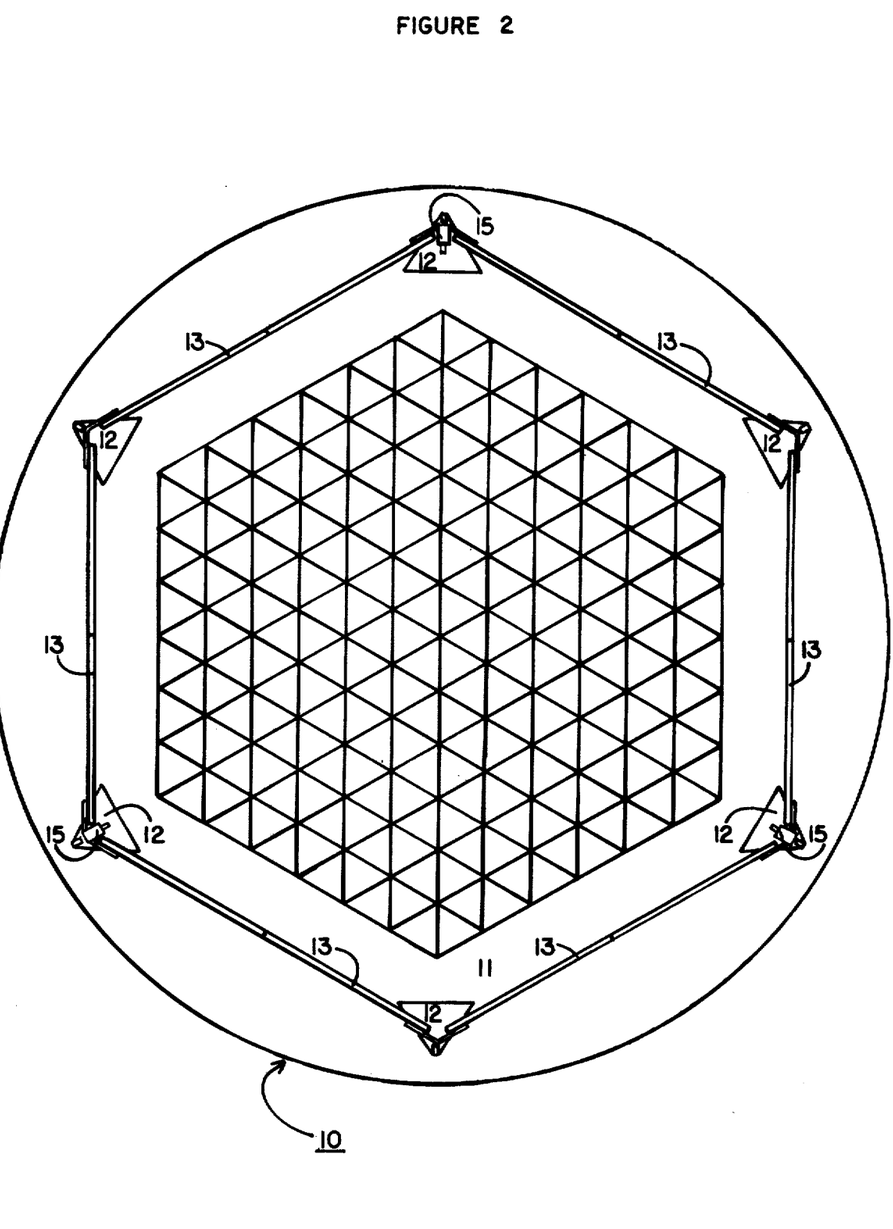
FIG. 2 is a top plan view of a preferred embodiment of the present invention.

Reference numeral 10 generally designates a behavioral and psychological test instrument permitting precise analysis of certain aspects of the individual and interpersonal behavior of individuals acted out within it in accordance with certain conditions specified by a qualified person. In general the device consists of (a) a circular floor 11, approximately 27 feet in diameter, made of cloth or heavy plastic sheeting with a pattern of equilateral triangles inscribed on it as shown in FIG. 2, on which rest (b) six identical vertical supporting members 12, shown in greater detail in FIGS. 3 and 4, which support (c) six identical horizontal supporting members 13, shown in greater detail in FIGS. 5 and 6, from which are hung (d) six identical curtains 14 made of a flexible white opaque material such as heavy plastic sheeting. These curtains 14 overlap by approximately two feet near each vertical supporting member 12, but the vertical sides of the curtains hang loosely and are not fastened together. This permits entry to the test instrument 10 near any of the six vertical supporting members 12 by pulling the curtains 14 apart, but, when undisturbed, the curtains 14 from walls completely enclosing the device without gaps or openings. If desired, one or more of the curtains 14 may be perforated for a window or viewing port 16 which would be covered by a piece of glass or plastic, coated so as to be partially reflecting, through which qualified observers standing outside the device could unobtrusively observe the behavior of people within the device. Motion picture or video cameras 15 may be mounted on one or more vertical supporting members, if desired, to record the behavior of people within the device. Alternatively, or in addition, three small loudspeakers, through which instructions may be given to people within the device without localizing the apparent source, may be mounted in the positions indicated in FIGS. 1 and 2 by reference numeral 15.

FIG. 2

This is a top plan view of the behavioral and psychological test instrument generally designated by reference numeral 10. Shown are (a) the pattern of equilateral triangles, each side of each such triangle being 0.5 meter (approximately 19.7 inches) in length, inscribed on the circular floor 11, (b) the positions of the six identical vertical supporting members 12 resting on the floor 11, (c) the positions of the six identical horizontal supporting members 13, supported by the vertical supporting members 12, and from which are hung the six identical curtains 14, as shown in FIG. 1, but which curtains 14 are not shown in FIG. 2, and (d) the motion picture or video cameras 15.

FIG. 3

Figure 3:
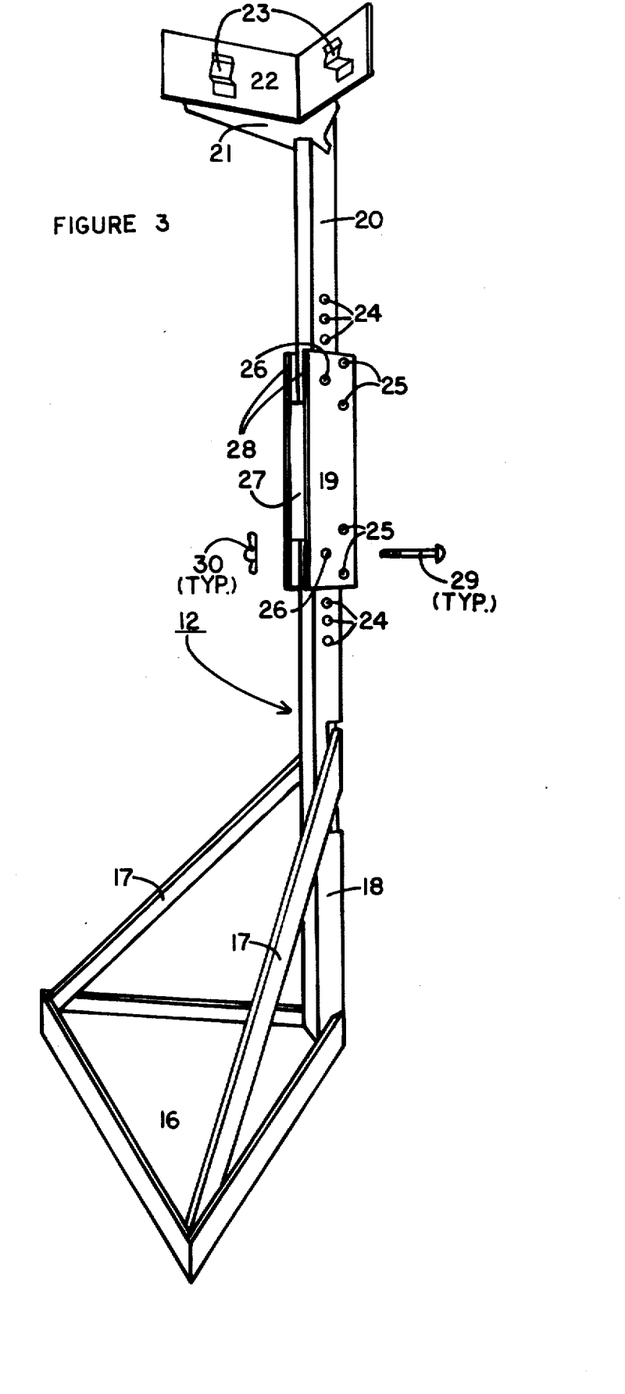
FIG. 3 is an oblique view, in perspective, of a vertical supporting member in the extended position.

Shown in an oblique perspective view is a vertical supporting member 12 in the extended position and ready for use. The vertical supporting member 12 is assembled from the following major components; (a) a triangular base 16 supporting (b) two braces 17, and (c) a lower upright member 18, which supports (d) a locking hinge assembly 19, to which is attached (e) an upper upright member 20 attached by (f) two brackets 21 (see FIG. 4) to (g) an angled face plate 22 which supports (h) two spring clips 23. The locking hinge assembly 19 consists of two side plates 28 attached to a spacer 27. Six holes 25 and 26 are drilled through each side plate 28 as shown. A number of holes 24 are drilled through the upper upright member 20 and the lower upright member 18 as shown. The vertical supporting member 12 is locked in the extended position as shown by six machine screws 29 inserted through the six holes 25 and 26 in the two side plates 28, and secured by six wingnuts 30. The two machine screws 29 inserted through the holes 26 in the two side plates 28 also pass through two holes 24, one in the upper upright member 20 and one in the lower upright member 18. The overall height of the vertical supporting member 12 can be adjusted by passing the two machine screws 29 that are inserted through the holes 26 in the two side plates 28 through different holes 24 in the upper upright member 20 or the lower upright member 18. The four machine screws 29 inserted through the holes 25 in the two side plates 28 pass immediately behind the upper upright member 20 and the lower upright member 18 and serve to lock the vertical supporting member 12 in the extended position by immobilizing the upper upright member 20 and the lower upright member 18 between the two side plates 28, and the spacer 27.

FIG. 4

Figure 4:
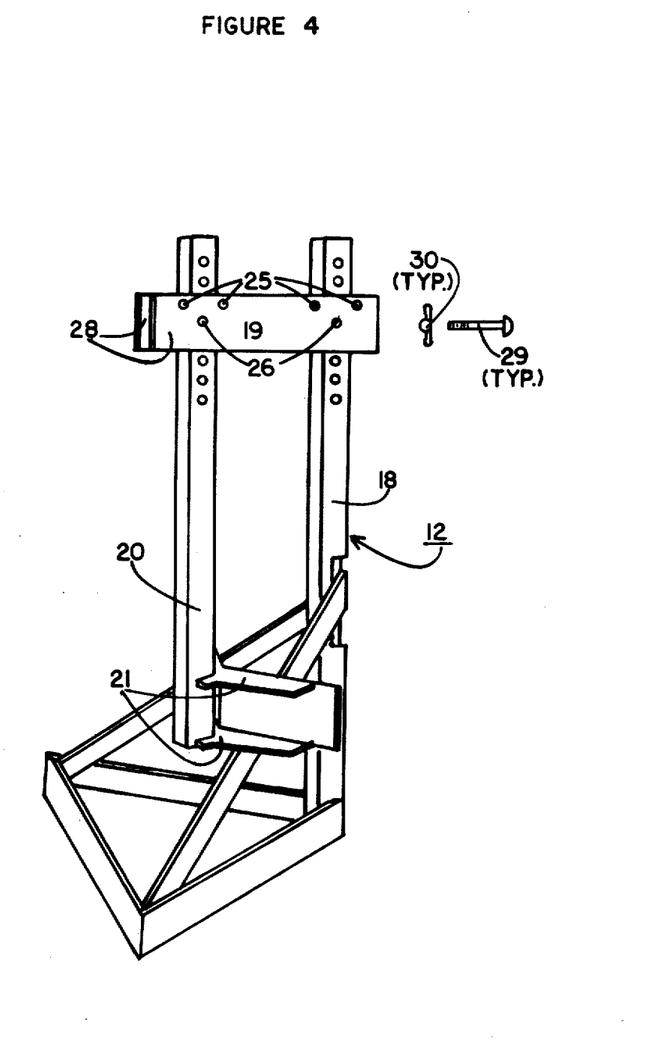
FIG. 4 is an oblique view, in perspective, of a vertical supporting member in the folded position.
Figure 5:
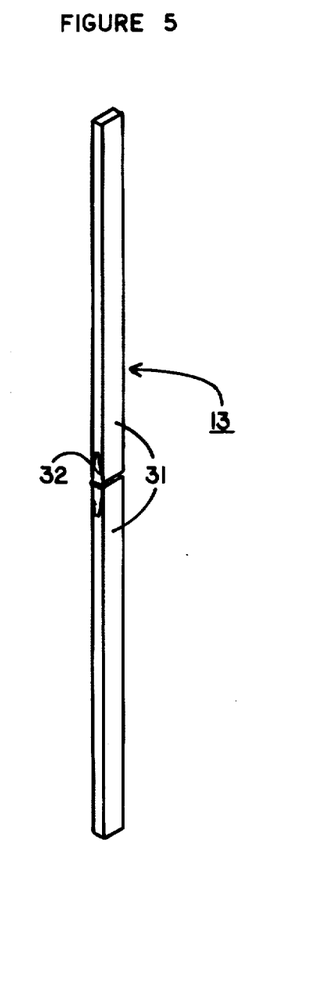
FIG. 5 is an oblique view of a horizontal supporting member in the extended position.

Shown in an oblique perspective view is a vertical supporting member 12 in the folded position ready for storage when not in use. The vertical supporting member 12 is shifted from the extended position shown in FIG. 3 to the folded position shown in FIG. 4 by removing the four machine screws 29 inserted into the holes 25 in the two side plates 28, which permits the upper upright member 20 and the lower upright member 18 to swing freely on the locking hinge assembly 19, supported by two machine screws 29 inserted through the holes 26 in the two side plates 28. Once the vertical supporting member 12 is positioned in the folded position as shown in FIG. 4, four machine screws 29 are inserted through holes 25, passing through the two side plates 28 and to either side of the upper upright member 20 and the lower upright member 18. The four machine screws 29 passing through the holes 25 in the two side plates 28 are then secured with four wingnuts 30, locking the vertical supporting member 12 in the folded position as shown in FIG. 4.

FIG. 5

Shown is an oblique view of a horizontal supporting member 13 in the extended position. The horizontal supporting member 13 consists of the two horizontal sections 31, to each of which is attached a butt plate 33 (shown in FIG. 6), and joined by a hinge 32. In use the horizontal supporting member, in the extended position, is supported at each end by a spring clip 23 (shown in FIG. 3) component of a vertical supporting member 12, as shown in FIG. 2. The hinge 32 being on the underside of the horizontal supporting member 13, which is supported at each end as indicated above, the horizontal supporting member 13 is held in the extended position by the force of gravity which locks the two horizontal sections 31 between the hinge 32 and the two butt plates 33 (shown in FIG. 6).

FIG. 6

Figure 6:
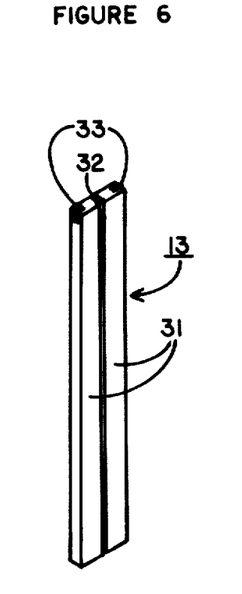
FIG. 6 is an oblique view of a horizontal supporting member in the folded position.

Shown is an oblique view of a horizontal supporting member 13 in the folded position ready for storage when not in use. The horizontal supporting member 13 consists of two horizontal sections 31, a hinge 32, and two butt plates 33.

FIG. 7

Figure 7:
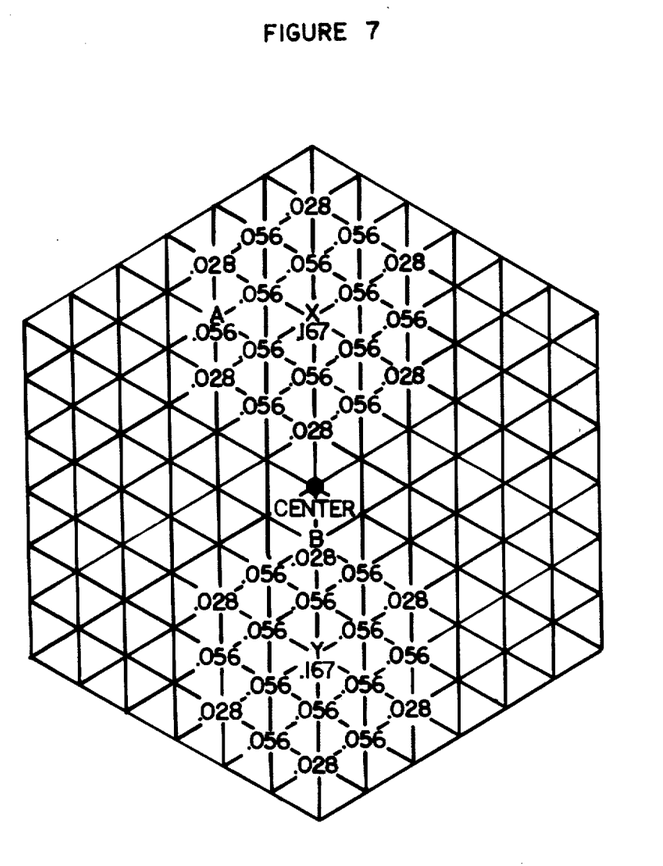
FIG. 7 is a view of the pattern on the floor of the device with certain "nodes" labelled to facilitate an explanation, in the text, of its properties.

Shown is a view of the pattern inscribed on the circular floor 11 (see FIGS. 1 and 2) of the behavioral test instrument 10 with certain parts of the pattern (referred to as "nodes" in the text) labelled with (a) words or (b) letters or (c) numbers representing probabilities which aid in describing the properties of this pattern in the text that follows, and which are referred to therein. These words, letters, and numbers are only used as an aid in describing the properties of the pattern and do not appear in the actual pattern on the circular floor 11, which has the appearance shown in FIG. 2.

The particular embodiment of the behavioral and psychological test instrument 10 shown in FIGS. 1 and 2 was chosen for a number of reasons. In general a setting for the study of human spatial behavior should have the following characteristics:

1. It should permit all sensory modalities of subjects to operate without obstruction.
2. Subjects should have enough space available to maintain any desired interpersonal distance.
3. Environmental and situational factors should be standardized or controllable in as much as this is possible.
4. There should be enough potential variability possible in the spatial behavior of experimental subjects to allow individual differences to manifest.
5. It should lend itself to analysis.

The first three of these requirements are met by the overall size and shape of the hexagonal room. The last two are met by the pattern of lines on the floor 11 of the instrument.

A variety of different patterns could be inscribed on the floor of a behavioral test instrument. Different patterns, as well as different overall sizes and shapes of the floor itself, could be useful for certain purposes. The pattern inscribed on the floor of the preferred embodiment, as illustrated in FIG. 2, was selected as the most generally suitable for the study of the way people use physical space in interpersonal interaction.

The method of analysis of behavior utilizing the pattern illustrated in FIG. 2 is described below in reference to "FIG. 7". However, the same general factors can be employed with other floor patterns, all of which are within the scope of this invention. In addition, particular considerations or test requirements may dictate the use of other patterns, all of which form different embodiments of this invention.

The pattern of equilateral triangles forming hexagons which cover the floor of the preferred embodiment of the device, as illustrated in FIG. 2, is known as a tesselation. Tesselations have been discussed by Martin Gardner in an article titled "On Tesselating the Plane with Convex Polygon Tiles" in *Scientific American*, Vol. 233, July 1975, pp. 112-117.

Imagine that you have an infinite supply of jigsaw puzzle pieces, all identical. If it is possible to fit them together without gaps or overlaps to cover the entire plane, the piece is said to tile the plane, and the resulting pattern is called a tessellation. (Gardner, p. 112).

Those points on a tesselation where two or more lines forming the pattern intersect are referred to as "nodes". Two nodes connected by a line forming the pattern, but not separated from each other by an intervening node are referred to as "adjacent nodes". In the most generally useful case, the behavior of interest within the device would be that of one or more experimental subjects each standing on a particular node, and moving to any adjacent node when instructed to do so by a qualified person or experimenter. The terms "node" and "adjacent node", and their use in the statistical analysis of the behavior of people within the device are described more fully below.

The problem of selecting the most generally useful tesselation for the study of the use of physical space in interpersonal interaction seems formidable since there are an infinite number of shapes that tile the plane. However, two characteristics of a pattern having broad usefulness can be identified. First, the distance between all adjacent nodes should be equal. Among other things, this justifies the assumption, used in the statistical analysis described below in reference to FIG. 7, that the probability of an experimental subject moving to any particular node adjacent to the one on which he or she is standing is the same as the probability of moving to any other adjacent node. If the distance between adjacent nodes were not equal, the problem of assigning a probability to any move between adjacent nodes would be complicated by possible preferences of subjects for "long" or "short" moves. Since not all subjects would be likely to share the same preference ordering, the assignment of probabilities to various longer or shorter moves would, itself, involve a probability distribution, thereby significantly complicating the interpretation of behavior in the instrument. However the use of long and short moves, while not considered desirable, is a realistic possibility and is considered to be within the scope of this invention.

A second characteristic in selecting a pattern is the "distance", as measured by the minimum number of moves from one adjacent node to another. Preferably, the "distance" that separates any two nodes should approximate the straight line distance between the same two nodes, as measured in arbitrary units one move long, as nearly as possible. This property is useful in a large number of possible experiments where the actual straight line distance between two experimental subjects is of interest.

From this disclosure, it is apparent that the preferred conditions for a pattern are obtainable by employing indicia, such as numeric, alpha-numeric, or design indicia, as the "nodes" with each indicia being spaced away a substantially equal distance from adjacent indicia. In this way, the general requirements detailed above are attained and a pattern of spaced indicia is achieved.

In addition, a pattern need not attain all of the preferred conditions and, instead, may comprise a plurality of polygons in spaced relationship with each other which are arranged in any type of statistically analyzable arrangement. Although such a pattern is not preferred due to the complexity of analyzing the test subject's movements, all such patterns are within the scope of this invention.

Except for numeric, alpha-numeric, or other similar indicia, the first condition, equal distances between all adjacent nodes immediately and by definition limits the shape of the "tiles" or pieces that can be considered to the regular polygons.

Let us being by asking how many of the regular polygons tile the plane. As the ancient Greeks knew and proved, there are just three: the equilateral triangle, the square and the regular hexagon. (Gardner, p. 112).

Since a pattern of regular hexagons can be obtained from the pattern described in this preferred embodiment by removing selected nodes and connecting lines, the pattern described in this preferred embodiment includes all the useful properties of a pattern of regular hexagons. In this manner, by applying the first characteristic of a generally useful pattern, the number of possible suitable tesselations has been reduced to two, the familiar checkerboard pattern of squares and the pattern described in this preferred embodiment.

The problem is now reduced to deciding between these two. To do this the second characteristic of a pattern having broad usefulness, that distance in "moves" between any two nodes approximate the straight line distance as nearly as possible, is invoked. This can be done by determining a ratio of the maximum and minimum straight line distances between all possible nodes separated by a fixed number of "moves". This ratio, defined as maximum straight line distance divided by minimum straight line distance between nodes separated by a fixed number of moves, is computed to be $1/\cosine 30° = 1.155$ for the pattern illustrated in this preferred embodiment, and $2 \times \cosine 45° = 1.414$ for the checkerboard pattern.

Since the ideal value of this ratio, which is unobtainable in practice, is 1,000, and since the ratio computed for the pattern illustrated in this preferred embodiment most closely approaches the ideal value, it has been shown that the pattern illustrated in this preferred embodiment is the best possible, given the two desired characteristics of such patterns that were established.

The overall shape of the floor in this preferred embodiment was chosen arbitrarily and other overall shapes may be useful for specialized purposes. Such other overall shapes can be obtained by using floors with different patterns inscribed on them, or by covering certain portions of the pattern shown in this preferred embodiment with a material similar to that on which the pattern is inscribed.

In addition, other lines can be added to the pattern shown in this preferred embodiment to delimit certain areas of this pattern or for other purposes.

As mentioned above, the points on the pattern where two or more lines intersect are referred to as "nodes" for convenience. An experimental run within the device could be described as a "game". In general, a game within the device would be "played" by one or more experimental subjects initially positioned by the experimenter so that they are standing on certain nodes such as those labelled X and Y in FIG. 7. The experimenter would then describe the rules of the game, which are the rules that subjects must follow in moving from node to node. To provide an example, assume that subjects can only move when instructed to do so by the experimenter, and can only move from the node on which they are standing to any adjacent node. An adjacent node is any node connected to the node a subject is occupying by a line, but not separated from it by another node. The distance between adjacent nodes is always 0.5 meter (approximately 19.7 inches). It can be seen by inspection of FIG. 2 that, unless the subject is standing on a node at the edge of the floor pattern, in which case the number of possible moves is reduced, he or she will have six possible moves to choose from each time they are instructed to move. To provide a simple example and avoid the complications introduced by "edge effects", suppose that a subject is initially positioned on the node at the center of the pattern (see FIG. 7) and makes five moves as described above. The total number of possible five move paths is then $6^5$ or 7776, indicating that even for relatively short games enough potential variety is available to satisfy requirement 4 above.

Requirement 5 provides the primary justification for using the game format described above for the study of human spatial behavior. A number of useful specialized probability distributions can be generated specifically for use with the instrument 10, and standard statistical techniques can be readily employed. An example may aid the reader to see how the specialized distributions are generated.

If, as a null hypothesis, it is assumed that subjects are making moves in a purely random manner, it is possible to determine the probability that a subject will reside on any node after any number of moves. This probability distribution, in the basic game described above, depends solely upon the subject's initial position and the number of moves. Two sample distributions for two subjects beginning the game in the initial positions indicated by X and Y in FIG. 7, for a two move game, are illustrated in FIG. 7. Further, since the probability of residing on any node is independent of the probability of residing on any other node, the probability of a subject residing on any set of combination of nodes is simply the summed probabilities associated with each individual node in the set.

Second, ignoring boundary effects occurring at the edge of the pattern (which mildly complicate the computations, but do not affect the basic analysis), each node is surrounded by a "ring" or six adjacent nodes arranged in a hexagonal pattern. Furthermore, this hexagonal pattern of nodes is surrounded by another concentric hexagon of twelve nodes, each being one move "outward" from the nodes forming the first hexagon. This second concentric hexagon is surrounded by a third hexagon of eighteen nodes, and so on until the boundary of the pattern is reached. These concentric hexagons are significant because a distinct minimum number of moves is required to reach the nodes on each hexagon from the node chosen as the initial position. This minimum number of moves, when multiplied by the length of a move (0.5 meter), is also a fairly good approximation of the actual physical distance between the initial position and any node on the appropriate concentric hexagon.

Combining these two observations, one can see how the game described above can be analyzed to determine whether the subjects' physical behavior indicates attraction to (or avoidance of) any node on the floor. Suppose that, after two moves, the subject who began the game standing on the node marked X is standing on the node marked A in FIG. 7, and the subject who began the game standing on the node marked Y is on node B. Further suppose that we want to know whether the subjects' behavior indicates that they are "attracted" to the center of the device. Node A is four moves from the center. The probability that the subject who began the game standing on node X will be less than or equal to four moves from the center, assuming random movement, is the sum of the probabilities attached, in the appropriate distribution, to all nodes four moves or closer to the center. The sum of these probabilities is $p=0.811$. This is interpreted as a probability of 0.811 that the subject who began the game standing on node X's "attraction" to the center is due to chance. However, the subject who began the game standing on node Y is only one move from the center. There is only one possible node with this property on which this subject could reside, the node marked B, and the probability associated with this node is $p=0.028$.

Perhaps more interesting, it is possible to determine the probability associated with the two subjects' separation from each other. Since this separation is a measure of their behavioral attraction to or avoidance of each other, the associated probability is a measure of whether any observed attraction or avoidance is due to chance. The required computations are somewhat more difficult than for the statistical measures described above, since they involve determining the joining distribution for the distance between subjects.

To see how this is done, think for a moment about the most extreme possible case of attraction, which would occur if the subject who began the game standing on node X and the subject who began the game standing on node Y in FIG. 7 were two moves apart. This can only occur when each subject is on one unique node, that closest to the center. (Note that for the subject who began the game standing on node Y this is the node labelled B.) The probability of residing on this node is 0.028 for each subject so the joint probability is $0.028 \times 0.028 = 0.001$, indicating that this would be expected to happen only once in 1000 two move games.

Similarly, one can compute the probability that the two subjects will be separated by three moves. There are eight possible combinations of positions for subjects who began the game on the nodes labelled X and Y that are separated by three moves in FIG. 7. It can then be seen that the associated probability is $(6 \times 0.028 \times 0.056) + (2 \times 0.056^2) = 0.016$, and the probability of a separation of three moves or less is $0.016 + 0.001 = 0.017$.

The probabilities associated with other separations can be computed, although the computations are tedious even for a two subject, two move game. However, the computational rules are relatively simple and the problem has been computerized.

The spatial and statistical properties of the pattern on the floor 11 of the behavioral test instrument 10 illustrated by the preceding example can be utilized in a number of ways to provide scientifically valid tests of various hypotheses about human spatial behavior.

It will thus be seen that the objects set forth above, among those made apparent from the preceding description, are efficiently attained and, since certain changes may be made in the above construction, without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A test chamber for observing and statistically evaluating human behavior comprising
   A. moveable wall member means positionable to peripherally surround and define a test chamber of any desired size and shape in any desired location;
   B. a test zone located within the wall members and defined by a specific pattern displayed on the floor of the chamber; and
   C. a test zone floor pattern comprising a plurality of indicia, with each indicia being in spaced relationship to adjacent indicia to provide a test subject with the plurality of alternate directions in which to move each time a move is required.

2. The test chamber defined in claim 1, wherein the distances between the plurality of indicia may be represented mathematically, whereby the specific movement of a test subject within the chamber in relationship to the specific floor pattern can be evaluated and analyzed in comparison to statistical probabilities.

3. The test chamber defined in claim 1, wherein the plurality of indicia are further defined as having substantially equal distances between each point at which a test subject is allowed to move.

4. A test chamber for observing and statistically evaluating human behavior comprising
   A. a plurality of independently moveable wall members positionable in adjacent, abutting relationship to each other to peripherally surround and define a test chamber of any desired size and shape in any desired location;
   B. a test zone positioned within the wall members and defined by a specific pattern displayed on the floor of the chamber; and
   C. a test zone floor pattern comprising a plurality of polygons, with each of the polygons being in line-sharing relationship with adjacent polygons, thereby establishing a pattern having a plurality of alternative moves available for each test subject each time a move is required;
   whereby the specific movement of a test subject within the chamber in relationship to the specific floor patterns can be evaluated and analyzed in comparison to statistical probabilities.

5. The test chamber defined in claim 4, wherein the polygons forming the test zone floor pattern are further defined as comprising identical shapes.

6. The test chamber defined in claim 5, wherein the polygons are further defined as being equilateral.

7. The test chamber defined in claim 6, wherein the plurality of equilateral polygons are further defined as comprising substantially equal distances between each common point at which two or more lines terminate and the next adjacent common termination point.

8. The test chamber defined in claim 4, wherein the test zone floor pattern comprises an overall shape in the form of a regular hexagon with its longest dimension being 7.5 meters (about 24.6 feet).

9. The test chamber defined in claim 4, wherein said chamber defining wall members are further defined as comprising a plurality of independent collapsible framework assemblies upon which opaque curtains are supportingly maintained, thereby providing the chamber defining wall members required for the test chamber.

10. The test chamber defined in claim 4, wherein the test zone floor pattern is inscribed upon sheet material which is removably positioned within the wall members in order to establish and display the test zone floor pattern.

11. The portable test chamber defined in claim 4, further comprising a plurality of identical, substantially vertical support members, each vertical support member comprising
   a. a base interconnected with and supportingly maintaining the vertical support member in its substantially vertical position,
   b. a hinge assembly mounted substantially midway along the vertical support member, thereby defining a lower vertical member and an upper vertical member, and
   c. cross member support means positioned near the top of the upper vertical member and incorporating bracket members for supportingly maintaining curtain bearing cross members.

12. The portable test chamber defined in claim 11, wherein the curtain holding rod members are further defined as comprising an elongated rod member having hinge means formed substantially midway along its length thereof, thereby providing an elongated rod which is easily folded into at least two sections.

13. The portable test chamber defined in claim 11, wherein said vertical support members are further defined as being constructed to supportingly maintain activity recording and monitoring apparatus.

14. The test chamber defined in claim 4, wherein any desired area of the test zone floor pattern can be effectively removed to eliminate an area from subject use.

15. The test chamber defined in claim 4, wherein objects are easily positioned on the test zone floor pattern for evaluating a subject's reaction thereto.

16. The test chamber defined in claim 4, wherein at least one of the chamber defining wall members incorporate a viewing port through which qualified observers outside the device can observe the behavior of people within the device.

17. A test chamber for observing and statistically evaluating human behavior comprising
   A. wall members peripherally surrounding and defining the chamber area;
   B. a test zone positioned within the wall members and defined by a specific pattern displayed on the floor of the chamber; and
   C. a test zone floor pattern comprising a plurality of equilateral hexagons, with each of said equilateral hexagons being formed by six equilateral triangles, thereby establishing a pattern having a plurality of alternative moves available for each test subject each time a move is required;
   whereby the specific movement of a test subject within the chamber in relationship to the specific floor patterns can be evaluated and analyzed in comparison to statistical probabilities.

18. The test chamber defined in claim 17, wherein each side of each equilateral triangle forming the test zone floor pattern comprises an overall length of about 0.5 meters or 19.7 inches.

* * * * *